US009212263B2

(12) United States Patent
Takamatsu et al.

(10) Patent No.: US 9,212,263 B2
(45) Date of Patent: Dec. 15, 2015

(54) REACTIVE IONIC LIQUID, AND ION-IMMOBILIZED METAL OXIDE PARTICLE, ION-IMMOBILIZED ELASTOMER, AND TRANSDUCER USING SAME

(71) Applicants: TOKAI RUBBER INDUSTRIES, LTD., Aichi-ken (JP); KYUSHU UNIVERSITY, NATIONAL UNIVERSITY CORPORATION, Fukuoka (JP)

(72) Inventors: Shigeaki Takamatsu, Hekinan (JP); Ryosuke Matsuno, Fukuoka (JP); Shingi Kumagai, Toyohashi (JP); Yota Kokubo, Kasugai (JP); Kazunobu Hashimoto, Nagoya (JP); Hitoshi Yoshikawa, Komaki (JP); Atsushi Takahara, Fukuoka (JP); Hideyuki Otsuka, Tokyo (JP)

(73) Assignees: SUMITOMO RIKO COMPANY LIMITED, Aichi (JP); KYUSHU UNIVERSITY, NATIONAL UNIVERSITY CORPORATION, Fukuoka (JP)

( * ) Notice: Subject to any disclaimer, the term of this patent is extended or adjusted under 35 U.S.C. 154(b) by 0 days.

(21) Appl. No.: 14/305,304

(22) Filed: Jun. 16, 2014

(65) Prior Publication Data

US 2014/0300247 A1 Oct. 9, 2014

Related U.S. Application Data

(63) Continuation of application No. PCT/JP2013/057438, filed on Mar. 15, 2013.

(30) Foreign Application Priority Data

Mar. 30, 2012 (JP) ................................. 2012-079230

(51) Int. Cl.
C07F 7/18 (2006.01)
C07F 9/54 (2006.01)
(Continued)

(52) U.S. Cl.
CPC ............ *C08G 77/442* (2013.01); *B81B 3/0032* (2013.01); *C07C 211/63* (2013.01);
(Continued)

(58) Field of Classification Search
CPC ....... C07F 7/1812; C07F 9/54; C07C 211/62; C07C 211/63
USPC ................... 562/114, 400; 556/427, 428, 437
See application file for complete search history.

(56) References Cited

U.S. PATENT DOCUMENTS 3,635,887 A 1/1972 Polmanteer
7,638,930 B1 12/2009 Kudoh
(Continued)

FOREIGN PATENT DOCUMENTS

CN 102276642 A 12/2011
CN 103429666 A 12/2013
(Continued)

OTHER PUBLICATIONS

STN Structure Search (Apr. 28, 2015).*
(Continued)

*Primary Examiner* — Vu A Nguyen
(74) *Attorney, Agent, or Firm* — Greenblum & Bernstein, P.L.C.

(57) ABSTRACT

A reactive ionic liquid to be used as an ionic component that is contained in an ion-containing layer in a transducer arranged in contact with a high-resistance layer as a dielectric layer of the transducer, and is restrained from migrating from the ion-containing layer to the high-resistance layer on application of a voltage is provided. The reactive ionic liquid comprises an ion pair that consists of an anion and a cation. In the reactive ionic liquid, (a) the anion comprises (a1) a reactive group that consists of an alkoxysilyl group and (a2) an anionic group consisting of a carboxylate ($-COO^-$) group or a sulfonate ($-SO_3^-$) group. (b) The cation (b1) consists of an imidazolium, ammonium, pyrrolidinium, morpholinium, or phosphonium cation, and (b2) does not comprise an N—H group or a P—H group.

3 Claims, 3 Drawing Sheets

(51) Int. Cl.
| | |
|---|---|
| C07C 211/63 | (2006.01) |
| C08G 77/442 | (2006.01) |
| C08K 9/06 | (2006.01) |
| C08L 21/00 | (2006.01) |
| C07D 233/00 | (2006.01) |
| C07C 311/48 | (2006.01) |
| B81B 3/00 | (2006.01) |
| C08F 279/02 | (2006.01) |
| F03G 7/00 | (2006.01) |

(52) U.S. Cl.
CPC ............ *C07C311/48* (2013.01); *C07D 233/00* (2013.01); *C07F 7/1836* (2013.01); *C07F 9/5407* (2013.01); *C08F 279/02* (2013.01); *C08K 9/06* (2013.01); *C08L 21/00* (2013.01); *F03G 7/005* (2013.01)

(56) References Cited

U.S. PATENT DOCUMENTS

| | | |
|---|---|---|
| 7,671,514 B2 | 3/2010 | Lee et al. |
| 8,350,448 B2 | 1/2013 | Nagai et al. |
| 2002/0122561 A1 | 9/2002 | Pelrine et al. |
| 2012/0133243 A1 | 5/2012 | Okuzaki et al. |
| 2013/0142548 A1 | 6/2013 | Suzuki et al. |
| 2013/0293063 A1 | 11/2013 | Takamatsu et al. |
| 2013/0296478 A1 | 11/2013 | Takamatsu et al. |

FOREIGN PATENT DOCUMENTS

| | | |
|---|---|---|
| JP | 2001-524278 A | 11/2001 |
| JP | 2003-506858 A | 2/2003 |
| JP | 2007-1959 A | 1/2007 |
| JP | 2009-286815 A | 12/2009 |
| JP | 2010-265235 A | 11/2010 |
| JP | 2010-265236 A | 11/2010 |
| JP | 2011-201104 A | 10/2011 |
| JP | 2011-213862 A | 10/2011 |
| WO | 01/06579 A2 | 1/2001 |
| WO | 2012/043303 A1 | 4/2012 |
| WO | 2013/054614 A1 | 4/2013 |

OTHER PUBLICATIONS

Japanese Office Action issued with respect to application No. 2014-507698, mail date is Mar. 17, 2015.

Vasko Jovanovski et al., "Dye-sensitized solar cells with electrolyte based on a trimethoxysilane-derivatized ionic liquid", Thin solid films, 511-512 (2006), 634-637.

Vasko Jovanovski et al., "Dye-sensitized solar cells with electrolyte based on a trimethoxysilane-derivatized iconic liquid", Thin Solid Films 511-512 (2006), pp. 634-637, pp. 635 Scheme 1.

Chinese Office Action issued with respect to application No. 201380009129.2, mail date is Jul. 29, 2015.

Extended European Search Report ossued with respect to application No. 13769746.2, mail date is Oct. 6, 2015.

Jinmei Miao et al., "Acetalization of carbonyl compounds catalyzed by acidic ionic liquid immobilized on silica gel", Journal of Molecular Catalysis A: Chemical, 348, 2011, pp. 77-82.

* cited by examiner

REACTIVE IONIC LIQUID, AND ION-IMMOBILIZED METAL OXIDE PARTICLE, ION-IMMOBILIZED ELASTOMER, AND TRANSDUCER USING SAME

CLAIM FOR PRIORITY

This application is a Continuation of PCT/JP2013/057438 filed Mar. 15, 2013, and claims the priority benefit of Japanese application 2012-079230, filed Mar. 30, 2012, the contents of which is expressly incorporated by reference herein in its entirety.

TECHNICAL FIELD

The present invention relates to a reactive ionic liquid, and an ion-immobilized metal oxide particle, an ion-immobilized elastomer, and a transducer using the same.

BACKGROUND ART

Transducers such as an actuator, a sensor, and a power generating device perform conversion between mechanical energy and electric energy. Another type of transducers such as a speaker and a microphone perform conversion between acoustic energy and electric energy. In order to form a highly flexible, compact, and lightweight transducer, polymer materials such as dielectric elastomers are useful.

For example, an actuator contains a dielectric layer formed of a dielectric elastomer and a pair of electrodes placed on both sides of a dielectric layer in the thickness direction. In the actuator, when a voltage applied between the electrodes is increased, an electrostatic attraction between the electrodes increases. The dielectric layer, placed between the electrodes, is thereby compressed in the thickness direction, leading to a reduced thickness of the dielectric layer. When the film thickness is reduced, the dielectric layer accordingly expands in a direction parallel to the electrode surfaces. On the other hand, when the voltage applied between the electrodes is reduced, the electrostatic attraction between the electrodes decreases. A compressive force applied to the dielectric layer in the thickness direction thereby decreases, and the film thickness increases due to the elastic restoring force of the dielectric layer. When the film thickness increases, the dielectric layer accordingly contracts in a direction parallel to the electrode surfaces. The actuator thus expands and contracts its dielectric layer, thereby actuates a member to be actuated.

In order to increase the force and displacement output from the actuator, it is preferable that the dielectric layer has a higher dielectric constant, higher resistance to dielectric breakdown, and higher flexibility. A higher dielectric constant allows the layer to accumulate more charges therein. Higher resistance to dielectric breakdown allows the layer to withstand a higher electric field. Higher flexibility allows the layer to be expanded and contracted repeatedly. A silicone rubber, which has high resistance to dielectric breakdown, and acrylic and nitrile rubbers, which have high dielectric constants, are frequently used to prepare the dielectric layer (see, for example, PTL1 and PTL2).

CITATION LIST

Patent Literature

PTL1: JP 2003-506858 A
PTL2: JP 2001-524278 A
PTL3: JP 2011-201104 A

SUMMARY OF INVENTION

Technical Problem

A silicone rubber has a backbone consisting of siloxane bonds, which provides a high electric resistance. Thus, a dielectric layer made of a silicone rubber is hard to be dielectrically broken down when a high voltage is applied to the layer. However, the silicone rubber has a low polarizability, and thus has a low dielectric constant. Consequently, when the dielectric layer of the actuator is made of the silicone rubber, the electrostatic attraction between the electrodes with respect to the applied voltage is low. It is therefore difficult to obtain desired force and displacement by application of a practical voltage.

Meanwhile, acrylic and nitrile rubbers have higher dielectric constants than the silicone rubber. Thus, when the dielectric layer is made of the acrylic or nitrile rubber, the electrostatic attraction between the electrodes with respect to the applied voltage is larger, compared to a case where the silicone rubber is used. However, the acrylic and nitrile rubber have lower electric resistances than the silicone rubber. Therefore, the dielectric layer is more susceptible to dielectric breakdown. Further, an electric current (i.e., so-called a leakage current) passes through the dielectric layer during voltage application, and thus electric charges are not prone to be stored in the vicinity of the interface between the dielectric layer and the electrodes. Despite the high dielectric constants of the acrylic and nitrile rubbers, therefore, the electrostatic attraction decreases, and thus a satisfactory force and displacement can not be obtained. Furthermore, there is a risk that when a current passes through the dielectric layer, the dielectric layer may be physically broken due to generated Joule heat.

Thus, it is difficult to realize a dielectric layer providing both excellent resistance to dielectric breakdown and a large electrostatic attraction with the use of a single material. A dielectric layer has been proposed which is made of a plurality of materials to provide both satisfactory generative force and satisfactory resistance to dielectric breakdown.

For example, PTL3 discloses a dielectric laminate that comprises an ion-containing layer and a high-resistance layer. The ion-containing layer contains an elastomer and an ion component, while the high-resistance layer contains an elastomer and has a higher volume resistivity than the ion-containing layer.

In the dielectric laminate disclosed in PTL3, however, there is a possibility that the high-resistance layer is subjected to dielectric breakdown since the ion component in the ion-containing layer easily migrates into the high-resistance layer. Thus, in the dielectric laminate, it is desired that the ion component is prevented from migrating into the high-resistance layer.

The present invention has been made in view of the problems described above, and an object of the present invention is to provide a reactive ionic liquid to be used as an ionic component that is contained in an ion-containing layer in a transducer arranged in contact with a high-resistance layer as a dielectric layer of the transducer, and is restrained from migrating from the ion-containing layer to the high-resistance layer on application of a voltage. Another object of the present invention is to provide an ion-immobilized metal oxide particle, an ion-immobilized elastomer, and a transducer, using the reactive ionic liquid.

Solution to Problem

To achieve the objects and in accordance with the purpose of the present invention, a reactive ionic liquid according to a preferred embodiment of the present invention comprises an ion pair that consists of an anion and a cation. In the reactive ionic liquid, (a) the anion has (a1) a reactive group that consists of an alkoxysilyl group and (a2) an anionic group consisting of a carboxylate (—COO⁻) group or a sulfonate (—SO₃⁻) group. (b) The cation (b1) consists of an imidazolium, ammonium, pyrrolidinium, morpholinium, or phosphonium cation, and (b2) does not have an N—H group or a P—H group.

The anion preferably has a structure represented by general formula (1) or (2).

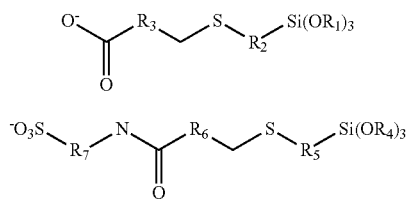

where $R_1$ to $R_3$ in formula (1) and $R_4$ to $R_7$ in formula (2) are straight-chain or branched alkyl groups.

The cation preferably has a structure represented by one of formulae (3) to (6).

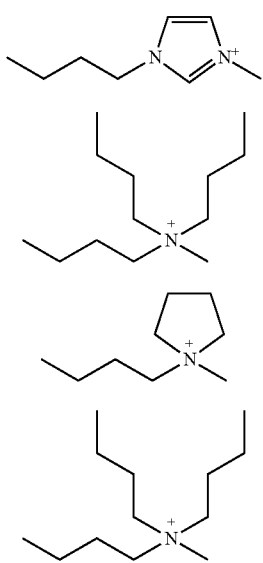

In another aspect of the present invention, an ion-immobilized metal oxide particle according to a preferred embodiment of the present invention contains the anion of the reactive ionic liquid described above and a metal oxide particle. The anion is immobilized to the metal oxide particle via a silanol group derived from the reactive group.

In another aspect of the present invention, an ion-immobilized elastomer according to a preferred embodiment of the present invention contains the ion-immobilized metal oxide particle described above and an elastomer that has a functional group that is reactive with a hydroxyl group contained in the ion-immobilized metal oxide particle. The ion-immobilized metal oxide particle is immobilized to the elastomer by a reaction between the hydroxyl group contained in the ion-immobilized metal oxide particle and the functional group contained in the elastomer.

In another aspect of the present invention, the transducer according to a preferred embodiment of the present invention contains a high-resistance dielectric layer that contains an elastomer and has a volume resistivity of $10^{12}$ Ω·cm or higher, a pair of positive and negative electrodes that are arranged on front and back sides of the high-resistance dielectric layer, and an ion-immobilized dielectric layer arranged between the high-resistance dielectric layer and the negative electrode. The ion-immobilized dielectric layer contains the ion-immobilized elastomer described above.

Advantageous Effects of Invention

Since the reactive ionic liquid according to the preferred embodiment of the present invention has the alkoxysilyl group as the reactive group in the anion, the anion can be immobilized to a metal oxide particle that has a hydroxyl group. The metal oxide particle to which the anion of the reactive ionic liquid is immobilized can be immobilized to an elastomer that has a functional group that is reactive with a hydroxyl group, by a reaction between the hydroxyl group contained in the ion-immobilized metal oxide particle and the functional group contained in the elastomer. Thus, the anion of the reactive ionic liquid is immobilized to the elastomer via the metal oxide particle. When an ion-containing layer that is in contact with a high-resistance layer as a dielectric layer in a transducer is made of the elastomer, the anion contained in the ion-containing layer is restrained from migrating into the high-resistance dielectric layer since the anion is immobilized to the reactive ionic liquid. Thus, dielectric breakdown of the high-resistance layer is suppressed.

DESCRIPTION OF EMBODIMENTS

Figure 1:
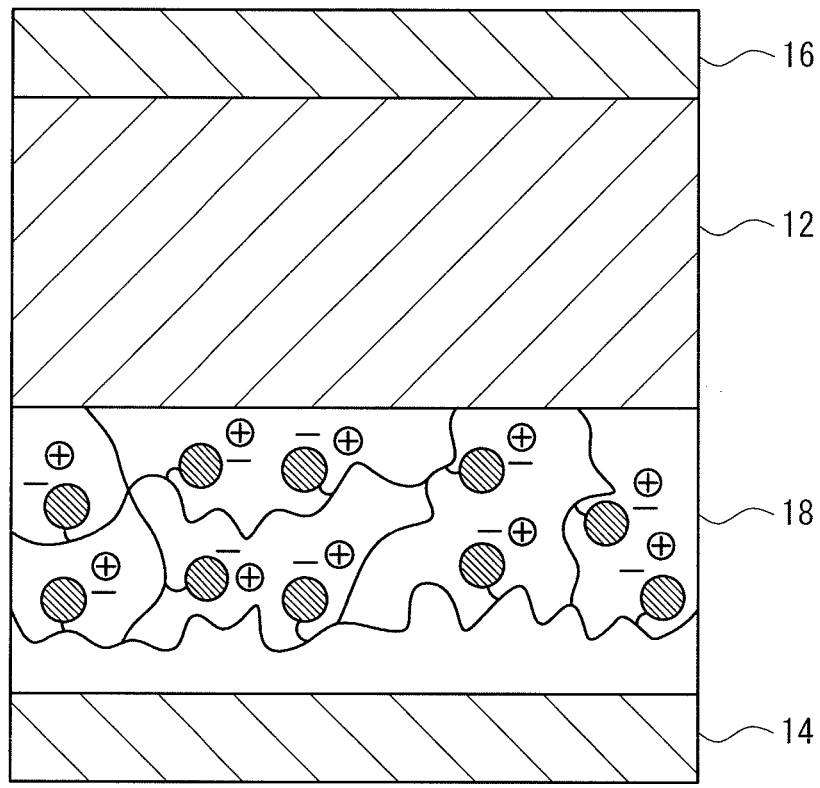
FIG. 1 is a schematic cross-sectional view showing a transducer according to a preferred embodiment of the present invention.

A detailed description of a preferred embodiment of the present invention will now be provided.

A reactive ionic liquid according to a preferred embodiment of the present invention contains an ion pair that consists of a specific anion and a specific cation.

The anion of the ionic liquid has an alkoxysilyl group (—Si(OR)₃) as a reactive group. The anion also has a carboxylic (—COO⁻) group or a sulfonate (—SO₃⁻) group as an anionic group.

Having the alkoxysilyl group as the reactive group, the anion of the reactive ionic liquid easily react with, for example, a compound having a hydroxyl group to form a silanol bond. Thus, the anion of the reactive ionic liquid, having the reactive group, can be immobilized to a metal oxide particle that has a hydroxyl group, via the silanol group.

Though the anion is not particularly limited as long as it has the reactive group and the anionic group, it is preferable that the anion of the reactive ionic liquid does not have a substituent group that tends to provide steric hindrance such as an aromatic ring in view of increasing the reactivity of the anion. It is also preferable that the anion has a small molecular weight. If the molecular weight is large, the reactivity of the reactive group is lowered, and electrophilic elements (such as oxygen) contained in the anion weakens the anionic charge. When the anionic charge is weakened, the anion becomes less bonded to the cation, and thus exhibits more ionic property. In view of these the molecular weight is preferably 500 or smaller, more preferably 450 or smaller, and still more preferably 400 or smaller. Though the lower limit of the molecular weight is not specifically determined, the molecular weight is preferably 250 or larger so that the anion can surely maintain the charge.

The anion preferably has a structure represented by general formula (1) or (2) below, for example.

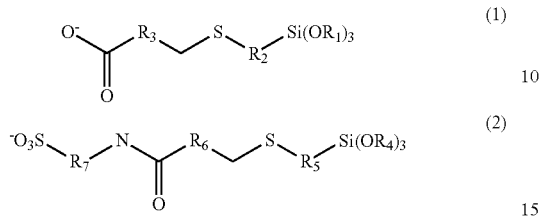

$R_1$ to $R_3$ in formula (1) represent straight-chain or branched alkyl groups. The number of carbon atoms in each of the alkyl groups is preferably within a range of 1 to 4. $R_4$ to $R_7$ in formula (2) represent straight-chain or branched alkyl groups. The number of carbon atoms in each of the alkyl groups is preferably within a range of 1 to 4.

Specific examples of the anion represented by formula (1) include one represented by formula (7). Specific examples of the anion represented by formula (2) include one represented by formula (8). Between them, the anion represented by formula (7) is more preferable, because, having a smaller molecular weight, the anion provides an ionic liquid that has a higher reactivity.

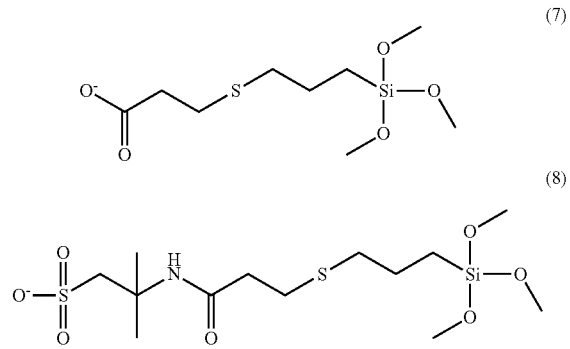

The cation of the reactive ionic liquid is selected from imidazolium, ammonium, pyrrolidinium, morpholinium, and phosphonium cations. Further, the cation does not have an N—H or P—H group.

Examples of an imidazolium cation having no N—H group include 1,3-dialkylimidazolium and 1,2,3-trialkylimidazolium cations. Examples of an ammonium cation having no N—H group include a quaternary ammonium cation. Examples of a pyrrolidinium cation having no N—H group include a 1,1-dialkylpyrrolidinium cation. Examples of a morpholinium cation having no N—H group include a 1-alkylmorpholinium cation. Examples of a phosphonium having no P—H group include a quaternary phosphonium cation.

If the imidazolium, ammonium, pyrrolidinium, and morpholinium cations have N—H groups, or if the phosphonium cation has a P—H group, the cations could not be isolated easily and thus could exhibit less ionic properties. Consequently, the cations could not provide ionic liquids.

Preferable examples of the cations include ones having structures represented by formulae (3) to (6) below. Among them, the cations represented by formulae (4) to (6) are more preferable because they have relatively high reactivities.

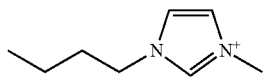

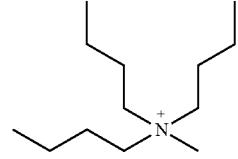

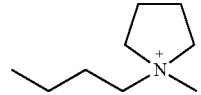

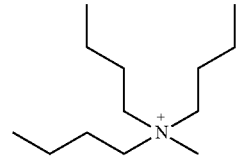

The reactive ionic liquid according to the preferred embodiment of the present invention may be prepared by an ene-thiol reaction between an ionic liquid monomer and a thiol compound having an alkoxysilyl group. The ionic monomer may be synthesized by an acid ester method or an anion exchange method. The ene-thiol reaction is an effective reaction in which side reactions are suppressed. Further, since a metal catalyst such as a platinum catalyst is not used in the ene-thiol reaction, there is no possibility that a metal atom remains in the obtained ionic liquid and affects properties of a product containing the reactive ionic liquid such as a transducer.

In the acid ester method, a monomer having a carboxylic or sulfonic acid structure is reacted to an ionic liquid that includes a carbonic acid ester as an anion. By the reaction, the anion is replaced with the monomer. In the anion exchange method, a monomer having a carboxylic or sulfonic acid structure is reacted to an ionic liquid that includes a halogen as an anion. By the reaction, the anion is replaced with the monomer. The anion exchange method may also be applied to a case in which the monomer is a sodium or potassium salt.

Reaction formula 1 shows a synthesis of an ionic liquid monomer by the acid ester method in which acrylic acid is used as the monomer having the carboxylic acid structure. Reaction formula 3 shows a synthesis of the ionic liquid monomer by the anion exchange method. Further, reaction formula 2 shows a synthesis of a reactive ionic liquid by the ene-thiol reaction of the obtained ionic liquid monomer and 3-mercaptopropyltrimethoxysiane as the thiol compound having the alkoxysilyl group.

(Reaction Formula 1)

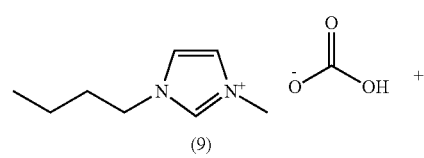

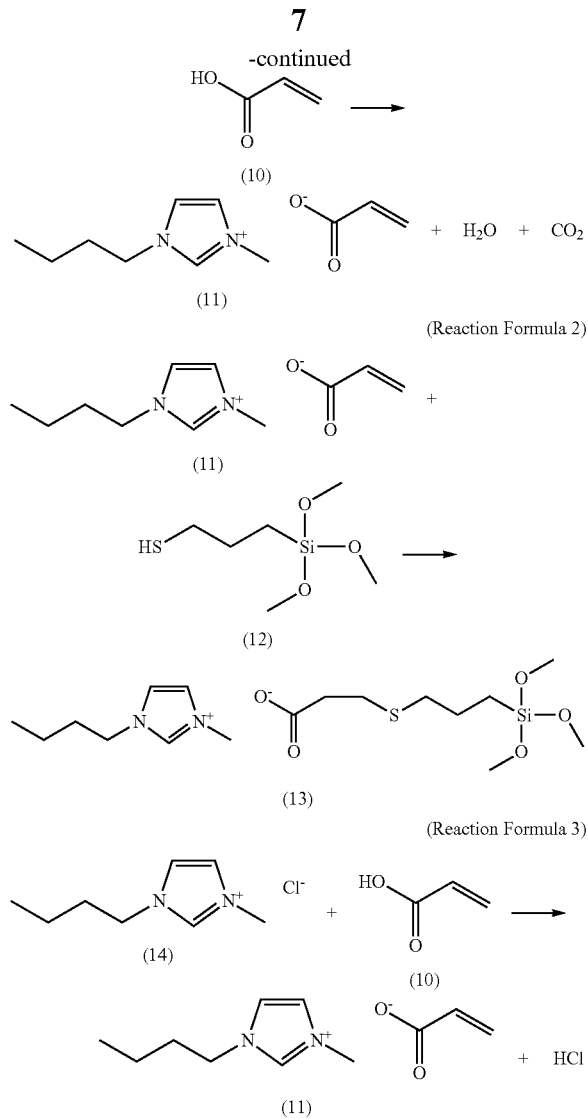

(Reaction Formula 2)

(Reaction Formula 3)

In reaction formula 1, the ionic liquid monomer (compound (11)) is synthesized from 1-butyl-3-methylimidazolium hydrogencarbonate (compound (9)) and acrylic acid (compound (10)). In reaction formula 3, the ionic liquid monomer (compound (11)) is synthesized from 1-butyl-3-methylimidazolium chloride (compound (14)) and acrylic acid (compound (10)). In reaction formula 2, the reactive ionic liquid (compound (13)) is synthesized from the ionic liquid monomer (compound (11)) and 3-mercaptopropyltrimethoxysilane (compound (12)).

In the acid ester method, which is represented by reaction formula 1, other compounds than the above-described compounds may be used: various ionic liquids having carbonic acid esters as anions and various monomers having carboxyl or sulfonic acid structures may be used.

Examples of the ionic liquids having carbonic acid esters as anions that may be used in the acid ester method shown in reaction formula 1 instead of compound (9) include 1,3-dimethylimidazolium hydrogencarbonate, 1-ethyl-3-methylimidazolium hydrogencarbonate, 1-butyl-3-methylimidazolium hydrogencarbonate, 1-ethyl-2,3-dimethylimidazolium methylcarbonate, triethylmethylammonium methylcarbonate, tributylmethylammonium methylcarbonate, tributylmethylphosphonium methylcarbonate, 1-butyl-1-methylpyrrolidinium methylcarbonate, 1-ethyl-1-methylpiperidinium methylcarbonate, and 4-ethyl-4-methylmorpholinium methylcarbonate (solution in methanol and water).

Examples of the monomers having carboxylic or sulfonic acid structures that may be used in the acid ester method shown in reaction formula 1 instead of compound (10) include methacrylic, 3-butenoic, 4-pentenoic, 5-hexenoic, 2-decenoic, 3-decenoic, 9-decenoic, 10-undecenoic, 3,7-dimetyl-6-octenoic, 2-methyl-4-pentenoic, 3-cyclopentene-1-carboxylic, propiolic, 2-butynoic, 2-hydroxy-3-butynoic, 5-hexynoic, 10-undecynoic, vinylsulfonic, and vinylphosphonic acids.

In the anion exchange method, as represented by reaction formula 3, other compounds than the above-described compounds may be used: various ionic liquids having halogen atoms as anions and various monomers having carboxyl or sulfonic acid structures may be used.

Examples of monomers having carboxylic or sulfonic acid structures that may be used in the anion exchange method shown in reaction formula 3 instead of compound (10) include the monomers listed above as examples of those used in the acid ester method shown in reaction formula 1.

Examples of the ionic liquids including halogens as anion that may be used in the anion exchange method shown in reaction formula 3, instead of compound (14), include 1-butyl-2,3-dimethylimidazoliumchloride, 1-butyl-2,3-dimethylimidazolium iodide, 1-ethyl-2,3-dimethylimidazolium bromide, 1-hexyl-2,3-dimethylimidazolium bromide, 1-hexyl-2,3-dimethylimidazolium chloride, 1-butyl-3-methylimidazolium bromide, 1-butyl-3-methylimidazolium chloride, 1-butyl-3-methylimidazolium iodide, 1,3-dimethylimidazolium chloride, 1,3-dimethylimidazolium iodide, 1,2-dimethyl-3-propylimidazolium iodide, 1-ethyl-3-methylimidazolium bromide, 1-ethyl-3-methylimidazolium chloride, 1-ethyl-3-methylimidazolium iodide, 1-hexyl-3-methylimidazolium bromide, 1-hexyl-3-methylimidazolium chloride, 1-hexyl-3-methylimidazolium iodide, 1-hexadecyl-3-methylimidazolium chloride, 1-methyl-3-n-octylimidazolium chloride, 1-methyl-3-n-octylimidazolium bromide, 1-methyl-3-propylimidazolium iodide, 1-octadecyl-3-methylimidazolium chloride, 1-butyl-1-methylpyrrolidinium bromide, 1-butyl-1-methylpyrrolidinium chloride, 1-butyl-1-methylpyrrolidinium iodide, tetrabutylammonium bromide, tetrabutylammonium chloride, tetrabutylphosphonium bromide, tetraoctylammonium bromide, tetrapentylammonium bromide, tributylhexadecylphosphonium bromide, 1-butyl-1-methylpiperidinium bromide, 1-butyl-4-methylpyridinium bromide, 1-butyl-3-methylpyridinium bromide, 1-butyl-3-methylpyridinium chloride, 1-butyl-4-methylpyridinium chloride, 1-butylpyridinium bromide, 1-butylpyridinium chloride, 1-ethylpyridinium bromide, 1-ethylpyridinium chloride, 1-hexylpyridinium bromide, 1-hexylpyridinium chloride, 1-allyl-3-ethylimidazolium iodide, 1-allyl-3-ethylimidazolium bromide, 1-allyl-3-methylimidazolium chloride, 1-allyl-3-methylimidazolium iodide, 1-allyl-3-butylimidazolium bromide, and 1,3-diallylimidazolium bromide.

Examples of thiol compounds having alkoxysilyl groups that may be used in the ene-thiol shown in reaction formula 2 instead of compound (12) include 3-mercaptopropyltriethoxysilane. As well as the compound having the trialkoxysilyl group, a compound having a monoalkoxysilyl group such as 3-mercaptopropylmethoxysilane and a compound having a dialkoxysilyl group such as 3-mercaptopropyl(dimethoxy)methylsilane may be used.

Next, a description of an ion-immobilized metal oxide particle according to a preferred embodiment of the present invention will be provided.

In the ion-immobilized metal oxide particle, the anion of the ionic liquid according to the preferred embodiment of the present invention is immobilized to a metal oxide particle via a silanol group derived from the reactive group.

The metal oxide particle, in view of having a high insulating property, preferably contains at least one element selected from titanium, zirconium, and silicon. Examples of the metal oxide particle include single oxide particles such as titanium dioxide ($TiO_2$), zirconium dioxide ($ZrO_2$), silica ($SiO_2$), and barium titanate particles. The examples also include composite oxides such as $TiO_2/ZrO_2$ and $TiO_2/SiO_2$ particles. The metal oxide particle is preferably prepared by hydrolysis of an organometallic compound (i.e., a sol-gel method) because the method facilitates formation of the ion-immobilized metal oxide particle.

The ion-immobilized metal oxide particle may be synthesized by a reaction of the metal oxide particle prepared by the sol-gel method with the reactive ionic liquid according to preferred embodiment of the present invention.

An organometallic compound may be used as a starting material for the sol-gel method. The organometallic compound used in the sol-gel method is preferably chelated. Chelating of the organometallic compound suppresses a rapid reaction of the organometallic compound with water, whereby metal oxide particles having a small diameter are produced without being aggregated.

The organometallic compound may be appropriately selected from metal alkoxide compounds and metal acylate compounds depending on the type of desired metal oxide particle. Examples of the metal alkoxide compounds include tetra-n-butoxy titanium, tetra-n-butoxy zirconium, tetra-n-butoxy silane, tetra-i-propoxy titanium, tetraethoxysilane, tetrakis(2-ethylhexyloxy) titanium, and titanium butoxide dimer. Examples of the metal acylate compound include polyhydroxy titanium stearate and zirconium tributoxy monostearate.

Examples of a chelating agent include a β-diketone such as acetylacetone, benzoylacetone, and dibenzoylmethane; a β-keto acid ester such as ethyl acetoacetate and ethyl benzoylacetate; triethanolamine; lactic acid; 2-ethylhexane-1,3-diol; and 1,3-hexanediol.

In the sol-gel reaction, the reactive ionic liquid, an organic solvent, and water are added to the chelated organometallic compound. The hydrolysis of the organometallic compound thereby proceeds to produce a metal oxide particle. The produced metal oxide particle has a hydroxyl group. The hydroxyl group reacts with the alkoxysilyl group, which is the reactive group of the anion of the reactive ionic liquid. By the reaction, the anion of the reactive ionic liquid is immobilized to the metal oxide particle via a silanol group. The anion is chemically bonded on a surface of or inside the metal oxide particle.

Examples of the organic solvent used in the sol-gel reaction include alcohols such as methanol, ethanol, and isopropyl alcohol (IPA); ketones such as methyl ethyl ketone (MEK) and methyl isobutyl ketone (MIBK); and ethers such as tetrahydrofuran (THF). For example, addition of IPA improves affinity between the chelated compound and water, so that a core for the metal oxide particle is easily produced.

The ion-immobilized metal oxide particle may be used to form a dielectric layer of a transducer or a solid polymer electrolyte, for example, when the particle is immobilized to an organic polymer such as an elastomer.

When used to form a dielectric layer of a transducer, the ion-immobilized metal oxide particle is preferably dispersed in the elastomer as uniformly as possible in view of transparency and resistance to dielectric breakdown of the dielectric layer. The diameter of the ion-immobilized metal oxide particle is preferably as small as possible. Thus, the median diameter of the metal oxide particle constituting the ion-immobilized metal oxide particles is preferably 5 nm or larger and 100 nm or smaller. The median diameter is more preferably 30 nm or less, and still more preferably in a range of about 10 nm to 20 nm. The diameter of the metal oxide particle may be measured through observation with a transmission electron microscope (TEM). Alternatively, the diameter may be measured by a small-angle x-ray scattering method.

The diameter of the metal oxide particle to be produced depends on the type and amount of the organic solvent used. For example, when a metal oxide particle having a median diameter of about 10 to 20 nm is to be produced, it is preferable that IPA and MEK may be mixed at a molar ratio IPA/MEK=0.6, approximately, while the amount of the IPA is seven to ten times, in molar ratio, of the amount of the organometallic compound. Water may be added as much as required for the hydrolysis of the organometallic compound.

When the metal oxide particle is produced by the hydrolysis of the organometallic compound, the diameter of the metal oxide particle in a sol and the diameter of the metal oxide particle in the dielectric layer are presumably identical. The diameter of the metal oxide particle in the sol may therefore be regarded as the diameter of the metal oxide particle in the dielectric layer. The diameter of the metal oxide particle in the sol may be measured with, a laser diffraction/scattering particle diameter/particle size distribution measurement apparatus, manufactured by Nikkiso Co., Ltd., for example. Alternatively, the diameter may be measured through observation with a scanning electron microscope (SEM) when the sol is dried.

The sol prepared by the hydrolysis of the organometallic compound contains the cation, which is a counterpart of the anion that has been immobilized to the metal oxide particle, as well as the ion-immobilized metal oxide particle.

The sol obtained may be subjected to an aging treatment. The aging treatment may be performed by leaving the sol for several hours at a temperature of about 40° C. The aging treatment reduces the number of the hydroxyl groups remaining inside the metal oxide particle, thereby suppressing the aggregation of the ion-immobilized metal oxide particles in the sol under storage.

Next, a description of an ion-immobilized elastomer according to a preferred embodiment of the present invention will be provided.

In the ion-immobilized elastomer, the ion-immobilized metal oxide particle is immobilized to an elastomer that has a functional group reactive with the hydroxyl group contained in the ion-immobilized metal oxide particle, by a reaction between the hydroxyl group in the ion-immobilized metal oxide particle and the functional group in the elastomer.

The ion-immobilized elastomer may be formed from the above-described sol that contains the ion-immobilized metal oxide and the cation, which is a counterpart of the anion immobilized to the metal oxide particle. Specifically, a mixed solution of the sol and the elastomer having the functional group reactive with the hydroxyl group in a solvent is applied onto a substrate and then heated. By the heating, the hydroxyl group on the surface of the ion-immobilized metal oxide particle reacts with the functional group in the elastomer, whereby the ion-immobilized metal oxide particle is immobilized (i.e., chemically bonded) to the elastomer. Thus, the ion-immobilized elastomer is obtained. In the ion-immobilized elastomer, the ion-immobilized metal oxide particle works also as a crosslinker to crosslink the elastomer. The elastomer may be crosslinked further by another crosslinker. Examples of the solvent to prepare the mixed solution include acetylacetone alone and a mixed solvent containing acetylacetone, as a main component, and a polar solvent such as 2-methoxyethanol, methyl ethyl ketone, methyl isobutyl ketone, and THF.

The elastomer is not particularly limited as long as it has a functional group reactive with a hydroxyl group. Examples of the functional group include a carboxyl group (—COOH), an amino group (—NH), and an epoxy group. For example, in view of having a high dielectric constant, preferable examples of the elastomer include a carboxylic-modified nitrile rubber (X-NBR) and a carboxylic-modified hydrogenated nitrile rubber (XH-NBR). Among them, an elastomer having an acrylonitrile content (i.e., AN bond amount) of 33 mass % or more is particularly preferable. AN bond amount is defined as a mass ratio of acrylonitrile with the entire mass of a rubber being 100 mass %.

The ion-immobilized elastomer may be used to form a dielectric layer of a transducer or a solid polymer electrolyte.

Next, a description of a transducer according to a preferred embodiment of the present invention will be provided.

The transducer contains a high-resistance dielectric layer, an ion-immobilized dielectric layer, and a pair of electrodes.

FIG. 1 shows an example of a layer structure of the transducer. The transducer 10 contains a high-resistance dielectric layer 12 and a pair of electrodes 14, 16, placed on the front and back sides of the high-resistance dielectric layer 12, respectively. An ion-immobilized dielectric layer 18 made of the ion-immobilized elastomer according to the preferred embodiment of the present invention is placed between the high-resistance dielectric layer 12 and the negative electrode 14. Meanwhile, the positive electrode 16 is in direct contact with the high-resistance dielectric layer 12 with no other dielectric layer placed between them.

The high-resistance dielectric layer 12 contains an elastomer and has a volume resistivity of $10^{12}$ Ω·cm or higher. The high-resistance dielectric layer 12 may be made of the elastomer alone, or may contain other ingredients in addition to the elastomer.

Examples of the elastomer constituting the high-resistance dielectric layer 12 include an ethylene-propylene-diene copolymer (EPDM), an isoprene rubber, a natural rubber, a fluoro rubber, a nitrile rubber (NBR), a hydrogenated nitrile rubber (H-NBR), a silicone rubber, a urethane rubber, an acrylic rubber, a butyl rubber, a styrene-butadiene rubber, an ethylene-vinyl acetate copolymer, and an ethylene-vinyl acetate-acrylic acid ester copolymer. The examples also include an elastomer modified by, for example, introduction of a functional group such as an epoxidized natural rubber and a carboxylic-modified hydrogenated nitrile rubber (XH-NBR). The elastomers may be used singly or in combination.

Examples of other ingredients contained in the high-resistance dielectric layer 12 include an inorganic filler that has a high insulating property. Addition of an insulating material increases the electric resistance of the high-resistance dielectric layer 12. Examples of the inorganic filler include silica, titanium oxide, barium titanate, calcium carbonate, a clay, a calcined clay, a talc, and a layered clay mineral. They may be used singly or in combination. For example, silica is preferable among them, because silica has a large number of the below-described functional groups, and because silica is relatively inexpensive. When silica, titanium oxide, or barium titanate is used, they may be prepared by hydrogenation (i.e., sol-gel reaction) of an organometallic compound.

In order to increase the insulating property of the high-resistance dielectric layer 12 by blocking a flow of electrons, it is preferable that the elastomer and the inorganic filler are chemically bonded to each other. To form the chemical bond, both the elastomer and the inorganic filler preferably have functional groups that are reactive with each other. Examples of the functional groups include hydroxyl (—OH), carboxyl (—COOH), and maleic anhydride groups. In this case, an elastomer modified, for example, by introduction of a functional group such as a carboxylic-modified hydrogenated nitrile rubber may be used preferably. Functional groups may be introduced to the inorganic filler or increased in number by selection of an appropriate production method or by surface treatment after produced. Having larger numbers of functional groups, the elastomer and the inorganic fillers have higher reactivity with each other.

The content of the inorganic filler may be determined in view of a factor such as volume resistivity of the elastomer. For example, the content is preferably 5 parts by mass or higher and 50 parts by mass or lower with respect to 100 parts by mass of the elastomer. When the content is lower than 5 parts by mass, the electric resistance of the layer 12 is not increased effectively. On the other hand, when the content is higher than 50 parts by mass, the layer 12 may be too hard to maintain sufficient flexibility.

The content of the ion-immobilized metal oxide particles in the ion-immobilized dielectric layer 18 is preferably 1 part by mass or higher and 10 parts by mass or lower with respect to 100 parts by mass of the elastomer. When the content is lower than 1 part by mass, the electrostatic attraction between the electrodes 14, 16 are not effectively increased. On the other hand, when the content is higher than 10 parts by mass, the effect of increasing the electrostatic attraction is saturated while so-called leakage current is increased.

It is preferable that the pair of electrodes 14, 16 can expand and contract following deformation of the high-resistance dielectric layer 12 and the ion-immobilized dielectric layer 18. Then, the deformation of the dielectric layers 12, 18 is hardly restricted by the electrodes 14, 16, and thus the transducer 10 tends to provide a desired output easily.

The material of the electrodes 14, 16 is not limited specifically. The electrodes 14, 16 may be made from a conductive paste or coating in which a conductive material is mixed in a binder such as an oil and an elastomer. Examples of the conductive material include a carbon material such as carbon black, Ketjen black, carbon nanotube, and graphene, and powders of a metal such as silver. Alternatively, the electrodes 14, 16 may be made of woven meshes of carbon fibers or metal fibers.

The transducer 10 may be produced as follows: a mixed solution to form the ion-immobilized dielectric layer 18 is applied onto a substrate, and then heated and crosslinked. Thus, the ion-immobilized dielectric layer 18 is prepared. The high-resistance dielectric layer 12 is prepared similarly: a solution to form the layer 12 is applied onto a substrate, and then heated and crosslinked. Next, The high-resistance dielectric layer 12 and the ion-immobilized dielectric layer 18 thus prepared are bonded to each other, and the substrates are peeled off. Thus, a laminate of the high-resistance dielectric layer 12 and the ion-immobilized dielectric layer 18 is prepared. Further, the electrodes 14, 16 are attached on the front and back sides of the laminate, whereby the transducer 10 is produced.

Figure 2:
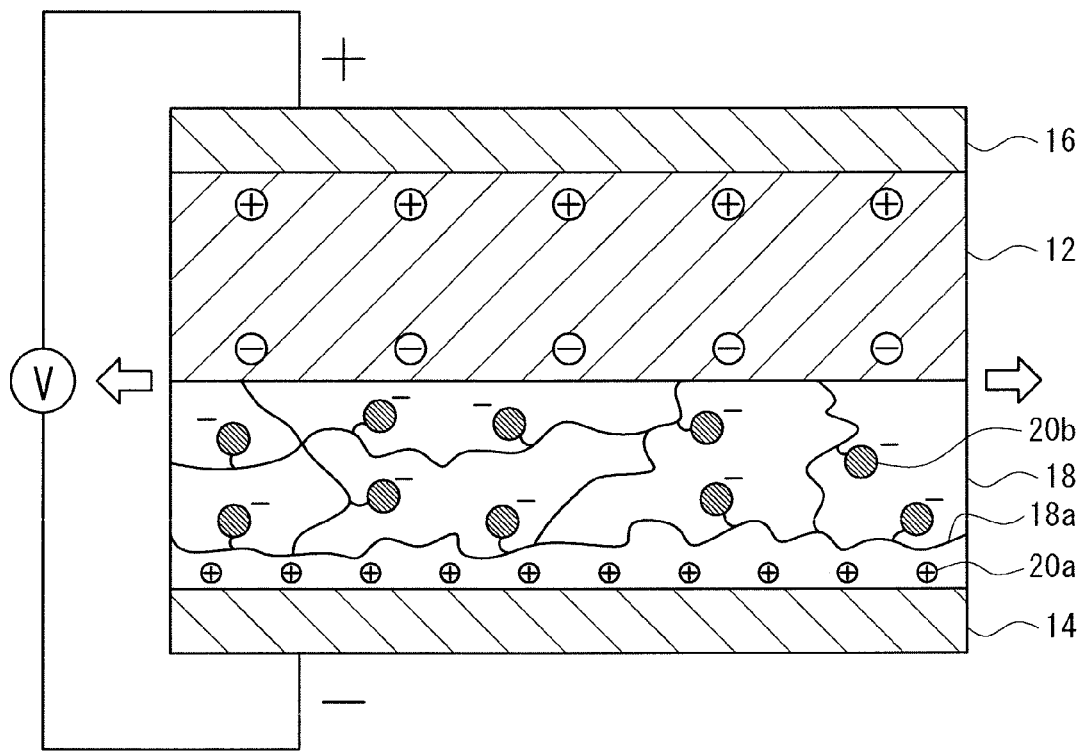
FIG. 2 is a schematic cross-sectional view showing the same during application of a voltage.

As illustrated in FIG. 2, when a voltage is applied between the positive electrode 16 and the negative electrode 14 of the transducer 10, the cations 20a of the reactive ionic liquid in the ion-immobilized dielectric layer 18 migrate toward the negative electrode 14. Meanwhile, the anion 20b of the reactive ionic liquid hardly migrates because the ion-immobilized metal oxide particles are bonded to the elastomer. In the high-resistance dielectric layer 12, positive electric charges are accumulated in the vicinity of the interface with the positive electrode 16 while negative electric charges are accumulated in the vicinity of the interface with the ion-immobilized dielectric layer 18, due to polarization. Thus, a large electrostatic attraction is generated between the positive electrode 16 and the negative electrode 14 that compresses the ion-immobilized dielectric layer 18 and the high-resistance dielectric layer 12. As a result, the ion-immobilized dielectric layer 18, and the high-resistance dielectric layer 12 are compressed between the electrodes 14, 16 while expanded along the planes of the dielectric layers 12, 18 as illustrated by the white arrow in FIG. 2.

Since the high-resistance dielectric layer 12 has a high electric resistance, the accumulated electric charges do not easily migrate within the high-resistance dielectric layer 12. Therefore, so-called leakage current is low, and generation of Joule heat due to the leakage current is suppressed. In the ion-immobilized dielectric layer 18, the anions 20b, having the same polarity as the adjacent negative electrode 14, are immobilized to the elastomer 18a via the metal oxide particle. Therefore, the anions 20b do not easily migrate toward the high-resistance dielectric layer 12 (i.e., toward a side opposite to the negative electrode 14).

Thus, since the ionic component in the ion-immobilized dielectric layer 18 consists of a reactive ionic liquid, the ionic component is immobilized to the elastomer 18a in the layer 18 via the metal oxide particle, whereby migration of the ionic component from the ion-immobilized dielectric layer 18 to the high-resistance dielectric layer 12 is suppressed. Consequently, decrease of the electric resistance and progress of degradation with time are suppressed in the high-resistance dielectric layer 12, whereby the high-resistance dielectric layer 12 maintains high resistance to dielectric breakdown.

In the transducer 10 described above, while the ion-immobilized dielectric layer 18 is placed between the high-resistance dielectric layer 12 and the negative electrode 14, the positive electrode 16 is in direct contact with the high-resistance dielectric layer 12 with no other dielectric layer between them.

In view of further increasing the electrostatic attraction between the electrodes 14, 16, ion-immobilized dielectric layers may be placed on both the front and back side of the high-resistance dielectric layer 12. In this case, a cation of an ionic liquid has to be immobilized in the ion-immobilized dielectric layer placed between the high-resistance dielectric layer 12 and the positive electrode 16 via a metal oxide particle. The ionic liquid may have a structure represented by formula (15), for example.

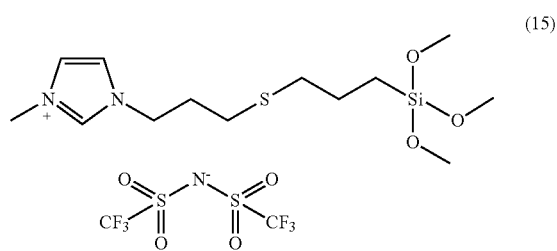

(15)

Transducers according to preferred embodiments of the present invention are not limited to the one illustrated above. For example, an ion-containing layer that contains a cation that is not immobilized to an elastomer may be placed between the high-resistance dielectric layer 12 and the positive electrode 16.

EXAMPLE

A description of the present invention will now be specifically provided with reference to examples.

Example 1

Synthesis of Reactive Ionic Liquid (13)

Acrylic acid monomer (0.0125 mol) was dropped into a 5.0 g solution of an equimolar amount of 1-butyl-3-methylimidazolium hydrogencarbonate (solvent: methanol/water=3:2 mixture; concentration: 50 mass %; 0.0125 mol) in an ice bath. During the dropping, generation of bubbles was observed. The reaction solution was returned to room temperature 30 minutes later, and was stirred for 6 hours. Then, the solvent was evaporated under a reduced pressure. After the evaporation, methanol (super dehydrated; manufactured by Wako Pure Chemical Industries, Ltd.) was added, and then evaporated under a reduced pressure. Thus, an ionic liquid monomer was obtained by the acid ester method. Subsequently, 2.10 g (10.0 mmol) of the obtained ionic liquid monomer and 1.87 mL (10.1 mmol) of 3-mercaptopropyltrimethoxysilane were dissolved in 20 mL of methanol (super dehydrated). 10 mol % of diisopropylamine with respect to the 3-mercaptopropyltrimethoxysilane was added to the solution as a catalyst. Then, the solution was stirred at room temperature for 20 hours. By evaporation of the reaction solution, reactive ionic liquid (13) represented by the formula below was obtained.

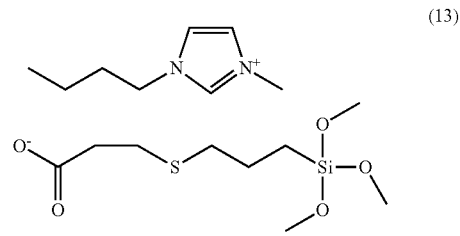

(13)

Example 2

Synthesis of Reactive Ionic Liquid (16)

Reactive ionic liquid (16) was synthesized in the same manner as reactive ionic liquid (13) except that a 9.75 g solution of 1-ethyl-1-methylmorpholinium methylcarbonate (solvent: methanol/water=2:3 mixture; concentration 50 mass %; 0.0238 mol) and an equimolar amount (0.0238 mol) of 2-acrylamide-2-methylpropane sulfonic acid were used in the synthesis by the acid ester method.

(16)

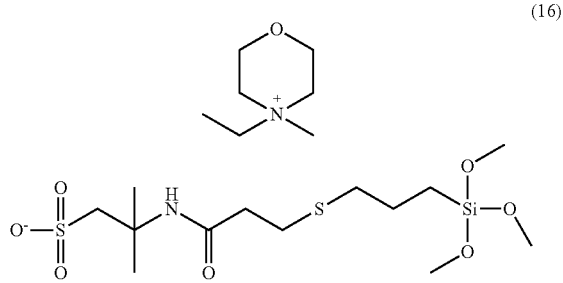

Example 3

Synthesis of Reactive Ionic Liquid (17)

Reactive ionic liquid (17) was synthesized in the same manner as reactive ionic liquid (13) except that a 10.11 g solution of tributylmethylammonium methylcarbonate (solvent: methanol/water=2:3 mixture; concentration 50 mass %; 0.0244 mol) and an equimolar amount (0.0244 mol) of 2-acrylamide-2-methylpropane sulfonic acid were used in the synthesis by the acid ester method.

(17)

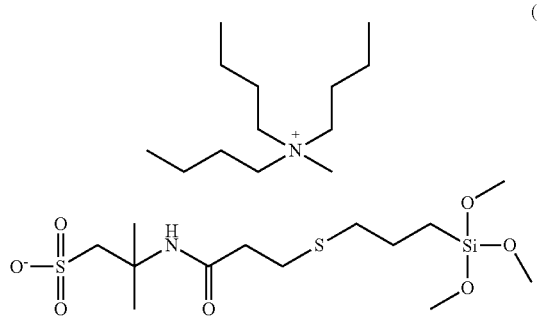

Example 4

Synthesis of Reactive Ionic Liquid (18)

Reactive ionic liquid (18) was synthesized in the same manner as reactive ionic liquid (13) except that a 10.64 g solution of 1-butyl-1-methylpyrrolidinium methylcarbonate (solvent: methanol/water=2:3 mixture; concentration 50 mass %; 0.0244 mol) and an equimolar amount (0.0244 mol) of 2-acrylamide-2-methylpropane sulfonic acid were used in the synthesis by the acid ester method.

(18)

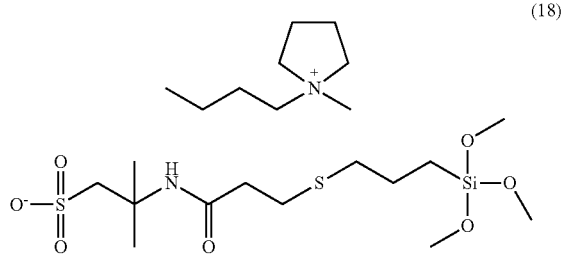

Example 5

Synthesis of Reactive Ionic Liquid (19)

Reactive ionic liquid (19) was synthesized in the same manner as reactive ionic liquid (13) except that a 15.11 g solution of tributylmethylphosphonium methylcarbonate (solvent: methanol/water=2:3 mixture; concentration 50 mass %; 0.0258 mol) and an equimolar amount (0.0258 mol) of 2-acrylamide-2-methylpropane sulfonic acid were used in the synthesis by the acid ester method.

(19)

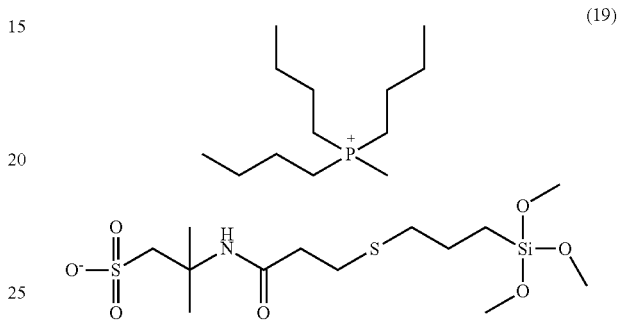

Example 6

Synthesis of Reactive Ionic Liquid (20)

Reactive ionic liquid (20) was synthesized in the same manner as reactive ionic liquid (13) except that a 10.00 g solution of 1-ethyl-1-methylmorpholinium methylcarbonate (solvent: methanol/water=2:3 mixture; concentration 50 mass %; 0.0244 mol) and an equimolar amount (0.0244 mol) of acrylic acid monomer were used in the synthesis by the acid ester method.

(20)

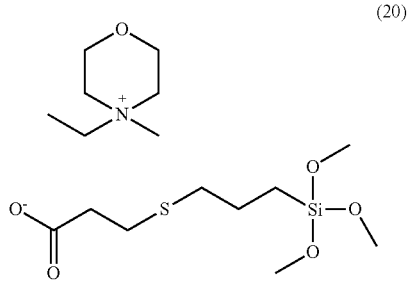

Example 7

Synthesis of Reactive Ionic Liquid (21)

Reactive ionic liquid (21) was synthesized in the same manner as reactive ionic liquid (13) except that a 10.95 g solution of tributylmethylammonium methylcarbonate (solvent: methanol/water=2:3 mixture; concentration 50 mass %; 0.0198 mol) and an equimolar amount (0.0198 mol) of acrylic acid monomer were used in the synthesis by the acid ester method.

(21)

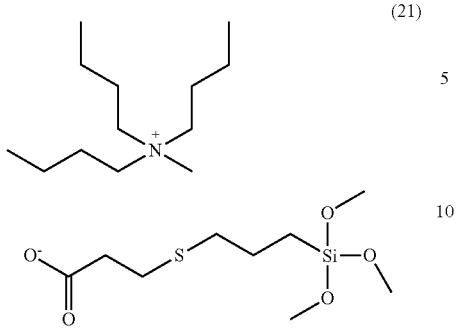

Example 8

Synthesis of Reactive Ionic Liquid (22)

Reactive ionic liquid (22) was synthesized in the same manner as reactive ionic liquid (13) except that a 10.14 g solution of 1-butyl-1-methylpyrrolidinium methylcarbonate (solvent: methanol/water=2:3 mixture; concentration 50 mass %; 0.0233 mol) and an equimolar amount (0.0233 mol) of acrylic acid monomer were used in the synthesis by the acid ester method.

(22)

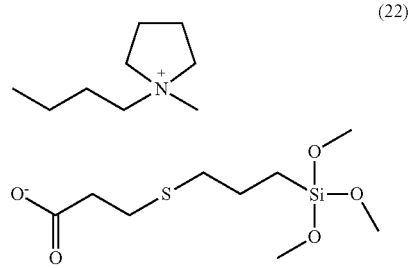

Example 9

Synthesis of Reactive Ionic Liquid (23)

Reactive ionic liquid (23) was synthesized in the same manner as reactive ionic liquid (13) except that a 15.11 g solution of tributylmethylphosphonium methylcarbonate (solvent: methanol/water=2:3 mixture; concentration 50 mass %; 0.0258 mol) and an equimolar amount (0.0258 mol) of acrylic acid monomer were used in the synthesis by the acid ester method.

(23)

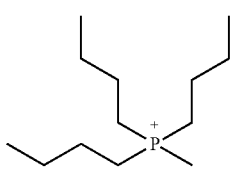

-continued

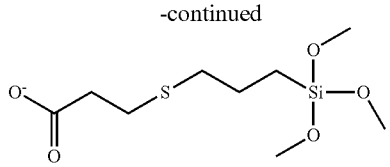

Example 10

Synthesis of Reactive Ionic Liquid (13)

10.0 g (0.057 mol) of 1-butyl-3-methylimidazolium chloride and 6.19 g (0.086 mol) of acrylic acid monomer were dissolved in 25 ml of distilled water. The solution was stirred at room temperature for 24 hours. Then the solvent was evaporated with a vacuum pump. Unreacted portion of the excessive amount of acrylic acid monomer was removed by rinsing with ethyl acetate. Thus, the ionic liquid monomer was obtained. Subsequently, the same ene-thiol reaction that was carried out in Example 1 was carried out in the same molar ratio.

Comparative Example 2

Synthesis of Ionic Liquid (24)

0.96 mL (10 mmol) of ethylimidazole and 2.07 g (10 mmol) of 2-acrylamide-2-methylpropane sulfonic acid were stirred in 40 mL of acetone at room temperature for 2 hours. Unreacted portion of 2-acrylamide-2-methylpropane sulfonic acid was removed by filtration. The filtrate was subjected to evaporation, and thus a viscous liquid compound was obtained. 3.00 g (10 mmol) of the obtained compound and 1.87 mL (10.1 mmol) of 3-mercaptopropyltrimethoxysilane were dissolved in 20 mL of methanol (super dehydrated; manufactured by Wako Pure Chemical Industries, Ltd.), and 4 mol % of diisopropylamine with respect to the 3-mercaptopropyltrimethoxysilane was further added to the solution. The solution was stirred at room temperature for 20 hours. By evaporation of the solvent, ionic liquid (24) was obtained.

(24)

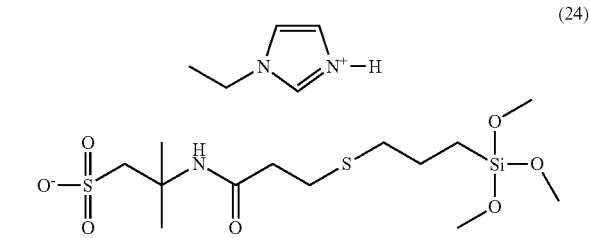

Comparative Example 3

Synthesis of Ionic Liquid (25)

Ionic liquid (25) was synthesized in the same manner as the ionic liquid according to Comparative Example 2 except that 3.36 mL (10 mmol) of trihexylamine was used instead of the ethylimidazole.

(25)

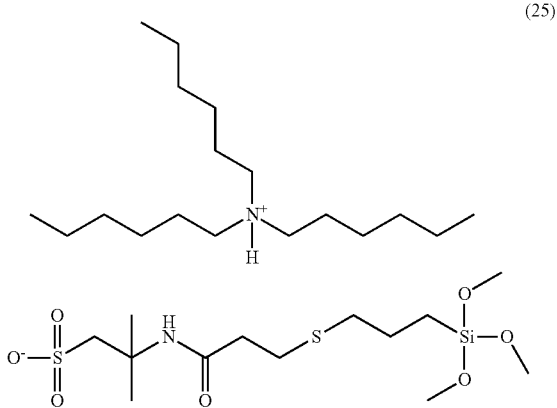

Comparative Example 4

Synthesis of Ionic Liquid (26)

25 mL (0.148 mol) of dimethylaminoethyl methacrylate was dissolved in 100 mL of acetone. A solution of 13 mL (0.148 mol) of propane sultone in 20 mL of acetone was dropped into the dimethylaminoethyl methacrylate solution under a nitrogen atmosphere. The mixed solution was stirred at room temperature for 14 hours. Then, a white precipitate was collected by filtration, and further was dried under a reduced pressure. Thus, a monomer was obtained. Next, 10 mmol of the obtained monomer and 10.1 mmol of 3-mercaptopropyltrimethoxysilane were dissolved in 50 mL of methanol. 4 mol % of diisopropylamine was further added to the solution. The solution was stirred at room temperature for 16 hours. By evaporation of the reaction solution, ionic liquid (26) was obtained. The ionic liquid was stored with trifluoroethanol mixed.

(26)

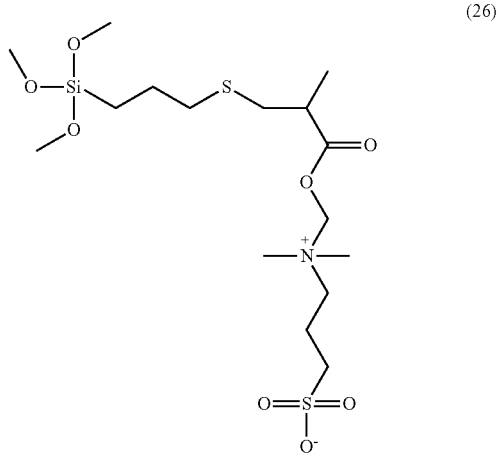

Synthesis of Ion-Immobilized Metal Oxide Particles

The obtained ionic liquids according to Examples 1 to 10 and Comparative Examples 2 to 4 were each resolved in 1:1 mixture (in molar ratio) of titanium tetraisopropoxide and acetylacetone. Isopropyl alcohol was further added to the solutions. Then, hydrolysis was carried out by dropping of water four times as much as the titanium tetraisopropoxide in molar ratio. Thus, sols in which anions of the ionic liquids are immobilized to titanium dioxide particles were obtained. A sample according to Comparative Example 1 was prepared in the same manner as the sample according to Example 1 except that no ionic liquid was added.

Synthesis of Ion-Immobilized Elastomer

The obtained sols according to Examples 1 to 10 and Comparative Examples 1 to 4 were each mixed in a 12-mass % solution of a carboxylic-modified hydrogenated nitrile rubber (HX-NBR; "Therban TX8889", manufactured by Lanxess) in acetylacetone so that the ion-immobilized metal oxide particles equivalent to 2.4 parts by mass of $TiO_2$ may be contained in the mixture with respect to 100 parts by mass of the HX-NBR. Further, 5 parts by mass of an acetylacetone solution of tetrakis(2-ethylhexyloxy) titanium (concentration: 20 mass %) was added to the mixtures as a crosslinker. The obtained mixed solutions were each applied onto substrates to form 9 μm thick films. The films were dried at 150° C. for an hour. Thus, ion-immobilized elastomers were obtained.

Preparation of Actuator

High-Resistance Dielectric Layer

A high-resistance dielectric layer was prepared as follows: first, 100 parts by mass of carboxylic-modified hydrogenated nitrile rubber ("Therban (trademark) XT8889", manufactured by Lanxess) and 10 parts by mass of silica ("Aerosil (trademark) 380", manufactured by Nippon Aerosil Co., Ltd.) were mixed and kneaded by a roll mill. Subsequently, the kneaded material was dissolved in acetylacetone. Then, 15 parts by mass of tetrakis(2-ethylhexyloxy) titanium, which is an organometallic compound, was added to the solution to prepare a liquid elastomer composition. The solid content of the obtained elastomer composition was 12 mass %. The acetylacetone here serves as a solvent for dissolving the carboxylic-modified hydrogenated nitrile rubber and also serves as a chelating agent for tetrakis(2-ethylhexyloxy) titanium. Subsequently, the elastomer composition was applied onto a substrate and dried, and then, heated at 150° C. for about 60 minutes. Thus, a high-resistance dielectric layer was obtained. The thickness of the high-resistance dielectric layer was about 20 μm, and the volume resistivity thereof was $2 \times 10^{12}$ Ω·cm.

(Preparation of Actuator)

In order to evaluate properties of the ion-immobilized elastomers according to Examples and Comparative Examples alone, a dielectric layer (dielectric film) consisting only of an ion-immobilized dielectric layer made of each of the above-prepared ion-immobilized elastomers was prepared, instead of a double-layered dielectric layer consisting of the high-resistance dielectric layer and the ion-immobilized dielectric layer. Carbon black was mixed and dispersed in an acrylic rubber polymer solution and dispersed to prepare a conductive coating. The conductive coating was screen-printed onto both the front and the back sides of the prepared dielectric layer to provide electrodes. Thus, an actuator was obtained.

For the dielectric materials (i.e., ion-immobilized elastomers) according to Examples and Comparative Examples, volume resistivities, dielectric constants, and actuator properties were evaluated. Methods and results of the evaluation are illustrated below.

(Volume Resistivity)

Volume resistivities of the dielectric materials were measured in accordance with JIS K6271 (2008). For the measurement, a direct-current voltage of 100 V was applied to the materials.

(Dielectric Constant)

The dielectric materials were each mounted on a sample holder ("12962A", manufactured by Solartron). Then, dielectric constants of the materials were measured with a dielectric interface ("1296", manufactured by Solartron) and a frequency response analyzer ("1255B", manufactured by Solartron) in combination (frequency: 100 Hz and 0.01 Hz).

(Actuator Property)

Figure 3:
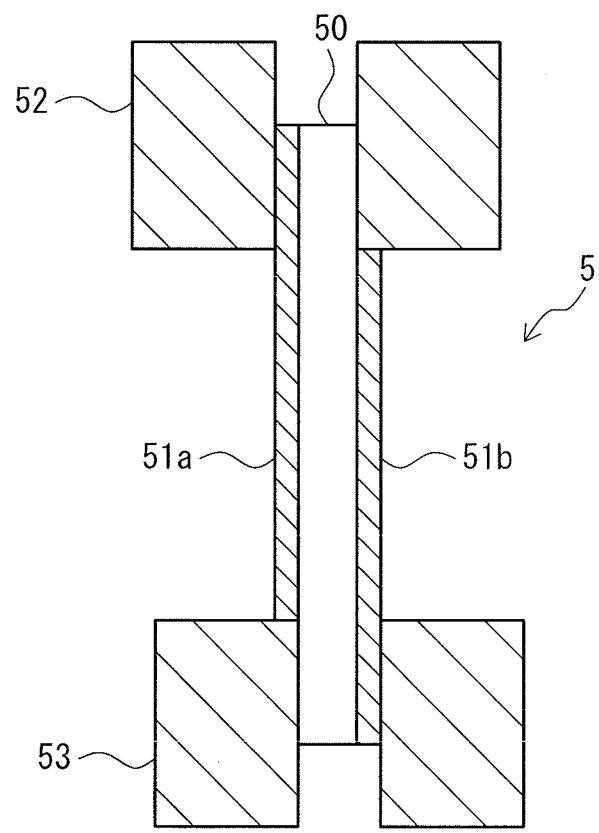
FIG. 3 is a cross-sectional view showing an actuator mounted on a measurement apparatus.

For the actuators prepared above, generative stresses were measured. The generative stresses, which represent actuator properties, were measured while a direct-current voltage with a field intensity of 30 V/μm was applied. FIG. 3 shows a cross-sectional view of an actuator mounted on a measurement apparatus.

As illustrated in FIG. 3, the upper end of an actuator 5 was held by an upper chuck 52 of the measuring apparatus. The lower end of the actuator 5 was held by a lower chuck 53. The actuator 5 was mounted between the upper chuck 52 and the lower chuck 53 while being extended in advance in the vertical direction (elongation ratio: 25%). A load cell (not shown) was arranged above the upper chuck 52.

The actuator 5 included a dielectric layer 50 and a pair of electrodes 51a, 51b. The electrodes 51a, 51b were arranged on the front and back sides of the dielectric layer, respectively, facing each other. Each of the electrodes 51a, 51b had a rectangular plate shape that was 40 mm long, 25 mm wide, and about 10 μm thick in a natural state. The electrodes 51a, 51b were arranged so as to be displaced from each other by 10 mm in the vertical direction. In other words, the electrodes 51a, 51b overlapped each other, via the dielectric layer 50, in an area of 30 mm long and 25 mm wide. An electric wire (not shown) was connected to the lower end of the electrode 51a. Similarly, an electric wire (not shown) was connected to the upper end of the electrode 51b. The electrodes 51a, 51b were connected to a power source (not shown) through the respective electric wires.

When a voltage was applied between the electrodes 51a, 51b, an electrostatic attraction occurred between the electrodes 51a, 51b to compress the dielectric layer 50. The dielectric layer 50 thereby decreased in thickness and expanded in the extension direction (i.e., in the vertical direction). Through the expansion of the dielectric layer 50, the extension stress in the vertical direction decreased. A decrease in the extension stress during the voltage application was measured with the load cell and was regarded as a generative stress.

(Generative Force after Extraction Treatment)

The actuators according to Examples, which exhibited high generative stresses in the above-described measurement, were immersed in ethanol, which can dissolve the ionic liquids, overnight. Then, the actuators are taken out of the ethanol, and rinsed with the ethanol. Generative stresses of the actuators were measured in the same conditions as above.

(Retention Rate)

Retention rates of the actuators were evaluated by comparison between the generative stresses before and after the extraction treatment.

TABLE 1

| | Example | | | | | | |
|---|---|---|---|---|---|---|---|
| | 1 | 2 | 3 | 4 | 5 | 6 | 7 |
| Polymer | 100 | 100 | 100 | 100 | 100 | 100 | 100 |
| Crosslinker | 5 | 5 | 5 | 5 | 5 | 5 | 5 |
| Titanium Oxide Particles | 2.4 | 2.4 | 2.4 | 2.4 | 2.4 | 2.4 | 2.4 |
| Reactive Ionic Liquid (13) | 1.04 | — | — | — | — | — | — |
| Reactive Ionic Liquid (16) | — | 1.36 | — | — | — | — | — |
| Reactive Ionic Liquid (17) | — | — | 1.54 | — | — | — | — |
| Reactive Ionic Liquid (18) | — | — | — | 1.39 | — | — | — |
| Reactive Ionic Liquid (19) | — | — | — | — | 1.58 | — | — |
| Reactive Ionic Liquid (20) | — | — | — | — | — | 1.02 | — |
| Reactive Ionic Liquid (21) | — | — | — | — | — | — | 1.20 |
| Reactive Ionic Liquid (22) | — | — | — | — | — | — | — |
| Reactive Ionic Liquid (23) | — | — | — | — | — | — | — |
| Ionic Liquid (24) | — | — | — | — | — | — | — |
| Ionic Liquid (25) | — | — | — | — | — | — | — |
| Ionic Liquid (26) | — | — | — | — | — | — | — |
| Volume Resistivity (Ω·cm) @ 100 V | $8 \times 10^{10}$ | $1 \times 10^{10}$ | $4 \times 10^{10}$ | $5 \times 10^{10}$ | $6 \times 10^{10}$ | $3 \times 10^{11}$ | $1 \times 10^{11}$ |
| Dielectric Constant (@ 100 Hz) | 11 | 11 | 11 | 11 | 12 | 12 | 12 |
| Dielectric Constant (@ 0.01 Hz) | 3800 | 1900 | 15700 | 6100 | 21300 | 1700 | 10200 |
| Generative Stress (A) (MPa) | 0.44 | 0.44 | 0.6 | 0.49 | 0.58 | 0.44 | 0.52 |
| Generative Stress after Extraction Treatment (B) (MPa) | 0.31 | 0.25 | 0.43 | 0.35 | 0.34 | 0.16 | 0.23 |
| Retention Rate (B/A) × 100(%) | 70 | 56 | 71 | 72 | 58 | 36 | 43 |

| | Example | | | Comparative Example | | | |
|---|---|---|---|---|---|---|---|
| | 8 | 9 | 10 | 1 | 2 | 3 | 4 |
| Polymer | 100 | 100 | 100 | 100 | 100 | 100 | 100 |
| Crosslinker | 5 | 5 | 5 | 5 | 5 | 5 | 5 |
| Titanium Oxide Particles | 2.4 | 2.4 | 2.4 | 2.4 | 2.4 | 2.4 | 2.4 |
| Reactive Ionic Liquid (13) | — | — | 1.04 | — | — | — | — |
| Reactive Ionic Liquid (16) | — | — | — | — | — | — | — |
| Reactive Ionic Liquid (17) | — | — | — | — | — | — | — |
| Reactive Ionic Liquid (18) | — | — | — | — | — | — | — |
| Reactive Ionic Liquid (19) | — | — | — | — | — | — | — |

TABLE 1-continued

| | | | | | | | |
|---|---|---|---|---|---|---|---|
| Reactive Ionic Liquid (20) | — | — | — | — | — | — | — |
| Reactive Ionic Liquid (21) | — | — | — | — | — | — | — |
| Reactive Ionic Liquid (22) | 1.04 | — | — | — | — | — | — |
| Reactive Ionic Liquid (23) | — | 1.24 | — | — | — | — | — |
| Ionic Liquid (24) | — | — | — | — | 1.29 | — | — |
| Ionic Liquid (25) | — | — | — | — | — | 1.74 | — |
| Ionic Liquid (26) | — | — | — | — | — | — | 1.16 |
| Volume Resistivity ($\Omega \cdot cm$) @ 100 V | $2 \times 10^{11}$ | $1 \times 10^{11}$ | $9 \times 10^{10}$ | $7 \times 10^{12}$ | $3 \times 10^{12}$ | $9 \times 10^{11}$ | $9 \times 10^{12}$ |
| Dielectric Constant (@ 100 Hz) | 13 | 12 | 12 | 11 | 12 | 12 | 12 |
| Dielectric Constant (@ 0.01 Hz) | 4800 | 13500 | 6000 | 14 | 16 | 24 | 16 |
| Generative Stress (A) (MPa) | 0.49 | 0.54 | 0.51 | 0.07 | 0.08 | 0.12 | 0.08 |
| Generative Stress after Extraction Treatment (B) (MPa) | 0.20 | 0.38 | 0.33 | — | — | — | — |
| Retention Rate (B/A) × 100(%) | 40 | 69 | 66 | — | — | — | — |

\* Reactive ionic liquid were synthesized by the acid ester method for Examples 1 to 9, and by the anion exchange method for Example 10.

The dielectric materials according to Examples 1 to 10 have much lower volume resistivities than the material according to Comparative Example 1, which indicates that the ionic liquids according to Examples 1 to 10 exhibit ionic properties. Further, the dielectric materials according to Examples 1 to 10 have high dielectric constants at the lower frequency. Meanwhile, the dielectric materials according to Comparative Examples 2 to 4 do not have such low volume resistances, which indicates that the ionic liquids according to Comparative Examples 2 to 4 hardly exhibit ionic properties. Further, the dielectric materials have low dielectric constants even at the lower frequency. The actuators according to Examples 1 to 10 have higher generative stresses than the actuator according to Comparative Example 1 while the actuators according to Comparative Examples 2 to 4 have almost the same generative stresses as the actuator according to Comparative Example 1. Thus, in the actuators according to Comparative Examples 2 to 4, addition of the ionic liquids in the actuator has little effects.

For the actuators according to Examples 1 to 10, which have high generative stresses, the generative stresses were measured also after the extraction treatment. According to the result, all of the actuators retain high generative forces even after the extraction treatment. This result indicates that the ionic liquids according to Examples 1 to 10 are immobilized to the metal oxide particles. Thus, it is confirmed that the immobilization of the ionic liquids suppresses migration of ions from the ion-immobilized dielectric layers to the high-resistance dielectric layers on application of the voltage. The actuators according to Examples 1, 3, 4, and 9 had high retention ratios, which indicates that the ionic liquids are immobilized to the metal oxide particles at especially high ratios. It is confirmed that having the specific configurations, the ionic liquids according to the preferred embodiment of the present invention provide large outputs.

The dielectric layer according to the preferred embodiment of the present invention is useful for an actuator, a sensor, and a power generating device, which perform conversion between mechanical energy and electric energy. The dielectric layer is also useful for a transducer of a speaker, a microphone, or a noise canceller, which perform conversion between acoustic energy and electric energy. It is particularly useful for a flexible actuator for: an artificial muscle for an industrial, medical, or welfare robots; a small-sized pump used for cooling of the electronic devices, or used in the medical field; and a medical instrument.

The foregoing description of the preferred embodiments of the present invention has been presented for purposes of illustration and description; however, it is not intended to be exhaustive or to limit the present invention to the precise form disclosed, and modifications and variations are possible as long as they do not deviate from the principles of the present invention.

The invention claimed is:

1. A reactive ionic liquid comprising an ion pair that consists of an anion and a cation, wherein
   (a) the anion comprises:
      (a1) a reactive group that consists of an alkoxysilyl group; and
      (a2) an anionic group consisting of a carboxylate (—COO⁻) group or a sulfonate (—SO$_3$) group, and
   (b) the cation:
      (b1) consists of an imidazolium, ammonium, pyrrolidinium, morpholinium, or phosphonium cation; and
      (b2) does not comprise an N—H group or a P—H group.

2. The reactive ionic liquid according to claim 1, wherein the anion has a structure represented by general formula (1) or (2):

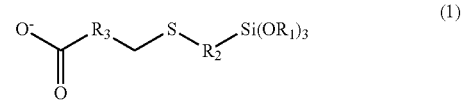

(1)

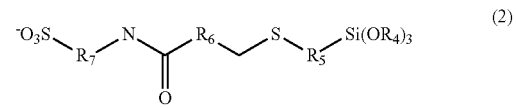

(2)

where $R_1$ to $R_3$ in formula (1) and $R_4$ to $R_7$ in formula (2) are straight-chain or branched alkyl groups.

3. The reactive ionic liquid according to claim 2, wherein the cation has a structure represented by one of formulae (3) to (6).

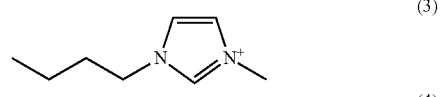

(3)

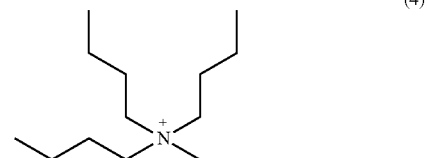

(4)

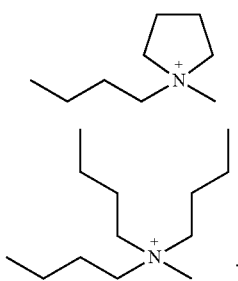
(5)
(6)
* * * * *